United States Patent [19]

Müller

[11] 4,088,539

[45] May 9, 1978

[54] PROCESS OF MANUFACTURING ENZYME PREPARATION RICH IN LIPASE

[75] Inventor: Klaus Peter Müller, Bergheim, Germany

[73] Assignee: A. Nattermann & Cie GmbH, Cologne, Germany

[21] Appl. No.: 793,322

[22] Filed: May 3, 1977

[30] Foreign Application Priority Data

May 7, 1976 Germany .............................. 2620289
Apr. 15, 1977 Germany .............................. 2716719

[51] Int. Cl.² ............................................ C07G 7/026
[52] U.S. Cl. ................................................. 195/66 R
[58] Field of Search ..................................... 195/66 R

[56] References Cited

U.S. PATENT DOCUMENTS 3,925,158  12/1975  Betzing et al. .................... 195/66 R

*Primary Examiner*—Lionel M. Shapiro
*Attorney, Agent, or Firm*—Karl W. Flocks

[57] ABSTRACT

Lipase is obtained by treating comminuted pancreas tissue with a mixture of 80 – 95% by volume (a) halogenated hydrocarbon having a boiling point of 47° – 130° C and a density greater than 1.3, or (b) hydrocarbon having a boiling point of 47° – 130° C and a density of from 0.655 to 0.88, and a water immiscible alcohol having 4 – 6 carbons.

4 Claims, No Drawings

PROCESS OF MANUFACTURING ENZYME PREPARATION RICH IN LIPASE

BACKGROUND

Ferment preparations comprising a high activity of digestive enzymes, especially lipase activity, are required for the treatment of the digestive-juice insufficiency in the gastric and intestinal tracts as well as in connection with indigestion. Fresh or deep-frozen pancreas tissue, in particular hog pancreas tissue is employed here as starting material. In order to keep as low as possible the charging of the organism with ineffective components in the preparations, the ferment activity of the products required for the preparation of the medicines should be as high as possible.

German Pat. No. 2,408,379 describes a process of preparing an enzyme preparation rich in lipase, wherein the comminuted pancreas tissue is first subjected to removal of fat with a mixture of 9 parts by volume chloroform and 1 part by volume butanol, whereafter the partly degreased tissue material is autolysed by being left standing at 0° – 4° C for 24–26 hours, then it is further degreased through a treatment with acetone, whereafter the enzyme is extracted with 5% aqueous ethanol solution and, through mixing with acetone, one obtains a precipitate from the extract. After drying, the precipitate represents a preparation comprising a high lipase activity.

According to an older proposal, as described in the German patent application No. P 25 05 887.1, the extract of effective substance obtained through extraction with the aqueous ethanol solution can also be transformed directly into a dry enzyme preparation through lyophilization. Although these substances are better than the previously known lipase preparations in regard to their activity, one must still strive always, both to simplify the process of preparation and also to increase the yield of enzyme from the glandular material and especially the activity of the obtained substances.

DESCRIPTION OF THE INVENTION

It has now been unexpectedly found that the required main degreasing of the comminuted pancreas tissue and the step of autolysis can be combined in a single stage, in which connection it is also possible to substantially shorten the duration of the autolysis.

According to the invention, one adds to the comminuted pancreas tissue an organic solvent mixture consisting of 80–95 volume % of (a) halogenated hydrocarbon, whose boiling point at normal pressure is between 47 and about 130° C and whose density should amount to more than 1.3 or (b) a hydrocarbon, whose boiling point at normal pressure is between 47° and about 130° C having a density of from 0.655 to 0.88 as well as 5–20 volume % of an alcohol comprising 4–6C atoms, which is substantially not miscible with water, the addition being performed during mixing in such an amount that a movable suspension is formed. The suspension of tissue thus obtained is then left standing at 15°–20° C for 12–40 hours, preferably 14–16 hours, during which the suspension may possibly be stirred a few times.

In the following the inventive process is described with reference to the use of a halogenated hydrocarbon.

During such autolysis, the cells of the gland release their aqueous cell content, which then forms an emulsion with the organic solvent mixture that is substantially not micsible with water. During the calm standing of the material, there are formed three layers, whereafter the central phase consisting of the emulsion of the albumincontaining tissue-liquid of the pancreas and the solvent mixture is separated in ordinary manner from the lower and upper phases. The upper phase consists here substantially of the degreased tissue fibers, while the lower phase consists substantially of the fat-containing solvent. By pressing out the isolated fibrous layer or through centrifugation, one can further increase the yield of emulsified tissue liquid up to 10%.

The combined emulsions are broken down through addition of acetone, in which connection one obtains a precipitate rich in lipase. After the precipitation, the enzyme concentrate is allowed to settle, the solution is decanted and the final product is washed repeatedly by stirring it in acetone. The product is separated by means of a screening device or a centrifuge, whereafter it is dried in vacuo and freed of solvent residue.

The grain-size distribution of the precipitate and, therewith, the bulk weight of the enzyme preparation can unexpectedly be influenced within certain limits through the rate of mixing the emulsion with acetone. In order to obtain a coarse-granular material, a layer of acetone is poured initially on the emulsion in an amount required for the precipitation and the two layers are then rapidly mixed with each other. On the other hand, a very fine grain can be obtained by adding acetone slowly during stirring.

A suitable halogenated hydrocarbons there may be mentioned, among other substances, trichlorotrifluorethane, which boils at about 47° C; the chlorohydrocarbons having a boiling point of up to 121° C; and mixtures of halogen hydrocarbons.

Trichloroethylene has turned out to be particularly advantageous in the organic solvent mixture for use in accordance with the invention, since the use of this chlorohydrocarbon not only leads to a particularly high activity of the obtained preparation, but the liquid mixture obtained after the completion of the process and consisting of halogen hydrocarbon, alcohol, acetone and water can also be readily separated through distillation. The recovery of solvents employed represents an important economic component precisely in the case of a process performed on a large industrial scale. It is well known that especially owing to the formation of azeotropes, many solvent mixtures can be separated only with difficulty during distillation and recovered in pure substance.

The employment of a chlorohydrocarbon having a density higher than 1.3 is of importance because it facilitates or makes possible the separation of the suspension in three desired phases during the process. The presence of a small amount of acetone in the organic solvent mixture has turned out as advantageous for the formation of the three layers.

As an alcohol which is substantially not miscible with water, n-butanol is especially suitable, but one can also use amyl alcohol and hexyl alcohol. These alcohols assist the freeing of the enzyme obtained in the central phase in accordance with the process of the invention.

The autolysis under degreasing conditions and the freeing of the enzyme from the cellular tissue can be promoted with a slight heating. Accordingly, in a preferred embodiment of the process, the autolysis is performed in two stages. Here the comminuted pancreas tissue is first mixed with the solvent mixture in an amount of 1–2 liters/kg gland material and treated at about 15° C for 14–16 hours. Then the settling fat-containing solvent. i.e., the lower layer, is separated as much as possible and the residue is again mixed with 1-2 liters solvent mixture per kg of tissue material, whereafter the temperature is increased to 20°-35° C, preferably 25°-30° C. After the material is stirred for about one hour, during which a powerful after-autolysis takes place, it is processed as previously described i.e., it is left standing and the central layer of emulsion is processed.

The process of the invention leads not only to a substantial simplification of the manufacturing procedure but also to preparations comprising increased enzyme activity. The combination of degreasing and autolysis with the organic solvent mixture provides the enzyme activity of the cellular tissue in the form of a highly concentrated emulsion, from which the enzyme can be directly precipitated. This eliminates the otherwise-required extraction steps, during which special solvents, e.g., aqueous alcohol or the like, are employed. The method of precipitating with the acetone also makes it possible to confer the desired degree of granulation to the enzyme powder during the precipitation, so that a subsequent granulation to larger particles is no longer necessary, when such larger particles are desired. The solvents to be employed in accordance with the invention also permit simple separation and recovery, which is of importance for operations carried out on large industrial scale.

When the halogenated hydrocarbon is replaced by an aromatic hydrocarbon, such as toluene (density 0.8716) or a paraffinic hydrocarbon, such as hexane (density 0.66) or heptane (density 0.681), and used in admixture with alcohol or alcohol and acetone the enzyme activity containing emulsion forms the lower phases. The advantage of this method consists in the fact that the use of the hydrocarbon solvent makes it possible to shorten substantially the autolysis and the time of degreasing in connection with an automation and, therewith, on the whole, a simplified recovery of the pancreas enzyme concentrate on large industrial scale. For example, the degreasing and autolysis can be performed in 4 hours at 15° C. A particular simplification consists in the more simple separation of the solids by means of a centrifugal decanter.

The invention is explained more in detail in the following non-limitative examples.

EXAMPLE 1

150 kg deep frozen pancreas is comminuted in a grinder-mixer to rice grain or lentil size and placed into a double-jacket container equipped with a stirrer. The jacket of the container is traversed by a flow of cooling water at 15° C.

The solids are mixed with 150 l trichloroethylene, which may contain up to 0.6% by weight acetone, and 25 l butanol-1 and the solids and the solvent are mixed with the stirrer. After about one hour the solids are thawed. The container is covered and the stirrer is run for 15 hours. Then the stirrer is stopped, the solids float up and the yellow, fat-containing solution situated thereunder is drained. The cooling water flowing through the container is replaced by a warm water of 30°-32° C, the solids are again mixed with 165 l of degreasing mixture and the mixture is stirred for one hour. During this time, the mixture reaches its final temperature of 28°-30° C. The stirrer motor is stopped and the emulsion and the solids are allowed to float up. A portion of the solvent in the form of a clear yellow solution is drawn off first and used for recovering the solvent. The brown emulsion flowing off thereafter is intercepted. The thick sludge discharged toward the end of draining is pressed out on a sieve-worm or screen screw press over a strainer or screen box. The material flowing out of the press is added to the emulsion.

The emulsion is placed back into the container equipped with stirrer, a layer of 1-1.5 liters of acetone per kg pancreas is poured on top of the emulsion, in which connection the acetone may be contaminated with up to 3% by weight of trichloroethylene, but with less than 1% water, and the two phases are mixed by starting the stirrer. After a period of 15 minutes, the stirrer is stopped. The product sinks in the form of solids to the bottom of the agitator vessel. The solution above the product is drawn off, the solids are suspended in 0.3-0.5 l acetone per kg pancreas for the purpose of washing, the material is stirred for five minutes, allowed again to settle and the solution is drawn off. The washing operation is performed all together 4-5 times, in which connection one may avoid using the settling procedure in the last washing step when a centrifuge is employed for separating the pancreatin. The paste of solid material may also be drained in a screen basket; of course, the losses of acetone are greater in such a case. The moist material is then dried in a vaccum shelf drier or drying cabinet at 45°-50° C and 30 torr or in a fluidized-bed drier at 50° C air inlet temperature and 40° C air outlet temperature. The material can be separated in various grain classes through screening. The finest grain can be agglomerated in a spray-type granulation; coarse grain can be comminuted through crushing. The following table shows the results of the test using glands of the same origin.

Table 1

Comparison of yield and lipase activity of pancreatin prepared in accordance with the prior state of the art and in accordance with this application.

PANCREATIN

| Origin of gland | Yield | Lipase activity (FIP-units/g) | Method of Preparation |
|---|---|---|---|
| A | 7.3 | 96,200 | Prior art |
| A | 10.1 | 100,000 | This invention |
| B | 6.3 | 71,000 | Prior art |
| B | 7.4 | 86,000 | This invention |
| C | 7.8 | 106,000 | Prior art |
| C | 10.1 | 119,000 | This invention |
| C | 9.2 | 120,000 | This invention |

Table 2

Comparison of bulk weight and grain-size distribution of pancreatin from glands of same origin while using different methods of acetone addition during precipitation.

| Yield (%) | Bulk weight (g/l) | Lipase activity (FIP-units/g) | Method of acetone addition during precipitation | Grain-size distribution 0.315 (%) | 0.315-0.800 (%) | 0.800 (%) |
|---|---|---|---|---|---|---|
| 9.4 | 360 | 84,000 |  | — | — | — |
| 10.1 | 417 | 93,000 | slowly during stirring | 98.1 | 1.2 | 0.7 |
| 11.5 | 440 | 76,000 |  | — | — | — |
| 9.8 | 463 | 93,000 |  | 97.5 | 2.1 | 0.4 |

Table 2-continued

Comparison of bulk weight and grain-size distribution of pancreatin from glands of same origin while using different methods of acetone addition during precipitation.

| Yield (%) | Bulk weight (g/l) | Lipase activity (FIP-units/g) | Method of acetone addition during precipitation | Grain-size distribution 0.315 (%) | 0.315–0.800 (%) | 0.800 (%) |
|---|---|---|---|---|---|---|
| 13.7 | 460 | 76,500 | method comprising poured-over layer | 46.4 | 52.6 | 1.0 |
| 12.9 | 514 | 81,500 | | — | — | — |
| 9.1 | 521 | 83,000 | | — | — | — |
| 14.6 | 482 | 79,200 | | 8.0 | 42.9 | 49.1 |

EXAMPLE 2

150 kg deep-frozen pancreas is comminuted in a grinder mixer as in example 1 and placed into a double-jacket vessel equipped with stirrer. The jacket of the vessel is traversed by a flow of cooling water at 15° C. The solids are mixed with 150 l methylene chloride and 15 l butanol-1 and degreased during stirring for 15 hours. Further 100 l methylene chloride is added to the mixture, which is well mixed, and the stirrer is shut off. The clear bottom phase is drained off. One adds again 150 l methylene chloride and 15 l butanol-l, the mixture is heated to 30° C (1 hour) an the clear solution-layer and the fibrous layer are separated.

After the fibers are pressed out, one obtains 140 l emulsion, which is cooled to 15° and 140 l acetone is poured over it in a layer. The emulsion and the acetone are mixed, the liquid is decanted from the settled pancreatin and, in accordance with example 1, one obtains a yield of enzyme concentrate at 9.3% in regard to the pancreas used.

Lipase activity of the enzyme concentrate: 86,500 FIP-units/g.

EXAMPLE 3

150 kg of deep-frozen pancreas is comminuted as in Example 1 and placed into an agitator vessel cooled to 15° C. One adds 150 l carbon tetrachloride an 15 l n-amyl alcohol to the material and the pancreas is degreased at 15° C (15 hours). One adds 75 l CCl$_4$ and 100 l acetone to the material, the stirrer is shut off and the fat-containing lower phase is separated. The mixture is then heated to 20° C, 15 l amyl alcohol and 150 l CCl$_4$ is again added to the material, which is stirred for 1 hour and 100 l emulsion is separated as in Example 1. One pours 100 l acetone in a layer over the emulsion and the enzyme concentrate is precipitated. After washing and drying, one obtains 10.1% of enzyme concentrate comprising 91,000 FIP-units/g of lipase activity.

EXAMPLE 4

150 kg deep-frozen pancreas is comminuted as in Example 1 and placed into an agitator vessel cooled to 15° C. One adds 15 l butanol-1 and 150 liter 1,1,1-trichloroethane and the degreasing is performed at 15° C (15 hours) while the material is stirred. One adds 75 l acetone to the material and the fat-containing solution is separated. One adds again 150 liter 1,1,1-trichloroethane, warms the material to 25° C and 100 l of emulsion is separated after 1 hour. One pours 100 l acetone in a layer over the emulsion and the enzyme concentrate is precipitated. After washing and drying, one obtains 9.8% yield of a product comprising 88,500 FIP-units/g lipase activity.

EXAMPLES 5 – 13

150 kg deep-frozen pancreas is comminuted and degreased in accordance with Examples 1-4. The type and amount of the degreasing solution used are shown in Table 3. This table likewise indicates a possible addition of V$_1$ liters of acetone subsequently to the first degreasing prior to the first separation of fibrous material and clear fat solution.

To the residue, one adds in each case 50 l halogen hydrocarbon and 15 l alcohol, the mixture is kept at t° C. for 1 hour and V$_2$ liters emulsion is obtained in accordance with Example 1. The emulsion is cooled to 15° C, V$_3$ liters of acetone is poured over it in a layer and the two are mixed. After washing with acetone, in accordance with Example 1, and drying, one obtains A % yield of enzyme concentrate comprising a lipase activity of B FIP-units/g. Table 3 contains all the numerical data.

Table 3

Use of different degreasing mixtures for obtaining pancreatin possessing high lipase activity.

| Example No. | Degreasing Mixture | Addition of acetone at the end of first degreasing V$_1$ (l) | Temperature during after-degreasing and autolysis t$_1$ (° C) | Amount of emulsion V$_2$ (l) | Amount of acetone used for precipitation V$_3$ (l) | Yield of pancreatin A (%) | Lipase activity B (FIP-units/g) |
|---|---|---|---|---|---|---|---|
| 5 | 150 l CCl$_4$ / 15 l butanol (1) | 0 | 31 | 185 | 305 | 10.2 | 90,000 |
| 6 | 150 l trichloroethylene / 15 l n-hexanol | 100 | 30 | 165 | 185 | 9.7 | 86,000 |
| 7 | 150 l trichloroethylene / 15 l butanol (1) | 0 | 28 | 145 | 160 | 9.9 | 88,000 |
| 8 | 150 l trichloroethylene / 15 l n-amyl alcohol | 90 | 30 | 150 | 150 | 10.5 | 87,500 |
| 9 | 150 l trichloroethylene / 30 l n-butanol | 0 | 28 | 150 | 150 | 10.8 | 90,500 |
| 10 | 150 l chloroform / 15 l n-butanol | 80 | 29 | 150 | 180 | 9.9 | 86,500 |
| 11 | 150 l trichloroethylene / 7.5 l n-butanol | 60 | 28 | 145 | 155 | 10.7 | 91,000 |
| 12 | 150 l trichloroethane / 15 l n-hexanol | 100 | 29 | 110 | 120 | 10.3 | 87,000 |

Table 3-continued
Use of different degreasing mixtures for obtaining pancreatin possessing high lipase activity.

| Example No. | Degreasing Mixture | Addition of acetone at the end of first degreasing $V_1$ (l) | Temperature during after-degreasing and autolysis $t_1$ (°C) | Amount of emulsion $V_2$ (l) | Amount of acetone used for precipitation $V_3$ (l) | Yield of pancreatin A (%) | Lipase activity B (FIP-units/g) |
|---|---|---|---|---|---|---|---|
| 13 | 150 l tetrachloroethylene 15 l n-butanol | 0 | 30 | 120 | 130 | 10.1 | 89,000 |

EXAMPLE 14

100 kg deep-frozen pancreas is comminuted to lentil size, mized with 75 liters toluene and 25 liters n-butanol and degreased for 4 hours with stirring in an agitator vessel surrounded by a flow of water at 15° C. The suspension formed is put into a centrifugal decanter and the solids are separated. The decantate is a white milk-like emulsion, which is precipitated with acetone. The precipitate is washed and dried.

Yield of enzyme concentrate; 10.0% in relation to pancreas.
Lipase activity: 81 000 FIP-units/g
Residual fat content: 0.052%
Bulk weight: 530 g/l

EXAMPLE 15

100 kg deep-frozen pancreas is comminuted to lentil size mixed with 75 liters of toluene or hexane, 15 liters of acetone and 20 liters of n-butanol, and degreased for 4 hours with stirring while warming to 15° C. The mixture is freed of the solids by means of a centrifugal decanter. The milky decantate is precipitated with acetone. The precipitate is washed and dried.

Yield of enzyme concentrate: 11.8% in relation to pancreas
Lipase activity: 77 000 FIP-units/g
Residual fat content: 0.022%
Bulk weight: 490 g/l It will be obvious to those skilled in the art that various changes may be made without departing from the scope of the invention and the invention is not to be considered limited to what is shown in the drawings and described in the specification.

What is claimed is:

1. In a process of manufacturing enzyme preparations rich in lipase from pancreas tissue through autolysis and degreasing of the comminuted tissue by means of a solvent mixture consisting of hydrocarbon and alcohol as well as precipitation of the enzyme from the aqueous phase through addition of acetone and drying of the precipitate, the improvement wherein the comminuted pancreas tissue is mixed in an organic solvent-mixture consisting of 80-95 volume percent of (a) a halogenated hydrocarbon, whose boiling point at normal pressure is between 47° and about 130° C and whose density amounts to more than 1.3, or (b) a hydrocarbon, whose boiling point at normal pressure is between 47° and about 130° C having a density of from 0.655 to 0.88, and 5-20 volume percent of an alcohol having 4-6 C atoms which is not miscible with water or a mixture of said alcohol and acetone, the solvent mixture being allowed to exert its effect on the tissue for 12-40 hours at 15°-20° C, the obtained tissue-water containing emulsion phase is separated from the other phases and a dry enzyme-preparation is obtained from said emulsion phase.

2. A process as in claim 1, wherein, after about 12-15 hour action of the halogenated hydrocarbon containing solvent mixture, the lower fat-containing solvent phase is removed and fresh solvent mixture is added again, then the material is stirred for about 1 hour at 20°-35° C, and is then allowed to settle prior to the processing of the central emulsion phase.

3. A process as in claim 1, wherein acetone is poured over the emulsion phase in a layer and the two are then mixed so quickly that a coarse-grained enzyme concentrate is precipitated.

4. A process as in claim 1, wherein the degreasing and autolysis with the mixture consisting of hydrocarbon and alcohol are performed at about 15° C for about 4 hours.

* * * * *